United States Patent [19]
Miller

[11] Patent Number: 5,151,163
[45] Date of Patent: Sep. 29, 1992

[54] ELECTROCHEMICAL NOISE MEASUREMENT TECHNIQUE FOR THE DETERMINATION OF ALUMINUM ALLOY PIT INITIATION RATES

[75] Inventor: James E. Miller, Middletown, R.I.

[73] Assignee: The United States of America as represented by the Secretary of the Navy, Washington, D.C.

[21] Appl. No.: 708,254

[22] Filed: May 26, 1991

[51] Int. Cl.⁵ .............................................. G01N 17/02
[52] U.S. Cl. ............................... 204/153.11; 204/404; 324/71.2; 324/700
[58] Field of Search ........................... 204/153.11, 404; 324/71.1, 71.2, 425, 700

[56] References Cited
U.S. PATENT DOCUMENTS 3,878,064  4/1974  Weisstuch et al. .............. 204/153.11
4,575,678  3/1986  Hladky ................................ 324/425

FOREIGN PATENT DOCUMENTS 2-128151  5/1990  Japan .............................. 204/153.11

Primary Examiner—Aaron Weisstuch
Attorney, Agent, or Firm—Michael J. McGowan; Prithvi C. Lall; Michael F. Oglo

[57] ABSTRACT

A technique is disclosed for using electrochemical noise (ECN) to characterize halide pitting reactions on a high strength aluminum alloy. ECN signals resulting from the pitting interaction of an aqueous halide solution with the oxide film on the aluminum alloy sample are measured. The signals are amplified, digitized, and then transferred to a digital computer where they are transformed from the time domain to the frequency domain by a fast Fourier transform function. Frequency spectrum amplitude data is then converted to a log-log scale thereby revealing a pattern of spectrum amplitudes indicative of pit initiation rates.

3 Claims, 6 Drawing Sheets

ELECTROCHEMICAL NOISE MEASUREMENT TECHNIQUE FOR THE DETERMINATION OF ALUMINUM ALLOY PIT INITIATION RATES

STATEMENT OF GOVERNMENT INTEREST

The invention described herein may be manufactured and used by or for the Government of the United States of America for Governmental purposes without the payment of any royalties thereon or therefor.

BACKGROUND OF THE INVENTION (1) Field of the Invention

This invention relates generally to electrochemical noise and more particularly to a method of using electrochemical noise for determining pit initiation rates for an aluminum alloy.

(2) Background of the Invention

The introduction of high-strength aluminum alloys during the past 40 years has solved many of the problems associated with reducing the weight of components formerly manufactured from ferrous alloys. A case in point is the use of aluminum alloy 6061 having the following composition.

| | |
|---|---|
| Magnesium | 1.0 |
| Silicon | 0.6 |
| Copper | 0.25 |
| Chromium | 0.25 |
| Aluminum | 97.9 |

Unfortunately, while these low density alloys have improved the strength-to-weight ratio desirable for many marine engineering applications, they also have brought with them their own unique set of corrosion problems. In particular, pitting corrosion in the marine environment is devastating for these alloys.

Corrosion resistance of an aluminum alloy results from the protective and tightly adherent aluminum oxide film which naturally forms on its surface. If this 50–100 angstroms thick film remains intact in an environment, corrosive breakdown cannot occur. Obvious sites for film breakdown are scratches or sharp discontinuities (where the film is mechanically stressed) and in regions where reactive ions speed up dissolution of the film. While the oxide film tends to repair itself if broken through, the environment or a pitting reaction itself may prevent it from reforming. Pitting corrosion of aluminum 6061, like that of other metal alloys, is associated with the flow of electric current between anodic and cathodic regions. The general mechanism by which this occurs is through the development of a corrosion cell or pit where oxidation and reduction reactions occur and are self-sustaining (autocatalytic).

There is depicted FIG. 1 in a cross-sectional diagrammatic illustration of a well-established pitting cell 15. Pitting cell 15 is shown in an aluminum alloy 10 that is exposed to an aqueous chloride environment or solution 100. Aluminum alloy 10, shown only in section, is comprised of an aluminum alloy base 11 and a corrosive-resistant aluminum oxide ($Al_2O_3$) film 13. Film 13 is naturally formed and is tightly adhered to the surface 11a of base 11. The surface 13a of film 13 is exposed to the aqueous chloride environment 100. A crust 14 of $Al(OH)_3$ precipitate forming over the pit 15 restricts solution 100 from entering the interior of pit 15. Accordingly, solution 100 enters the pit 15 only through a pore, designated generally by 14a, in the crust 14. The growth of the pit 15 involves the interaction of the aluminum base 11 directly with the solution 100 within the pit 15.

Note that exposed noble precipitates 17 can support oxygen reduction as an inert cathodic surface and thus provide cathodic protection for the areas immediately surrounding them. Noble precipitates 17 are local "islands" of precipitate alloy formed during the alloy solidification process. They are "noble" from the standpoint of being more corrosion resistant than the surrounding homogeneous alloy structure. They serve as discontinuities in the atomic lattice structure which inhibit the movement of lattice dislocations in order to strengthen the alloy 10. Pitting thus confines itself to specific areas of the alloy surface while adjacent surfaces remain virtually unaffected. This accounts for the non-uniform nature of pitting corrosion. Ultimately, it is the depletion of oxygen within the restricted confines of the pit 15 that allows the reaction to continue and precludes the formation of oxide film 13. This is evidenced by the predominance of other reduction reactions within the pit 15.

Pit conditions are transient as concentrations of ions necessary to support pitting reactions can be swept away by local solution currents and mixing. This in fact has been observed to occur, with the passive film 13 then reforming over a former pit location. The transient nature of pitting corrosion cells thus offers insight into the origin of electrochemical noise (ECN) signals. The pitting attack on the aluminum base 11 is observed, not as a steady and smooth reaction, but as an erratic and discontinuous process where the electric potential across the film 13 rises and falls as the reaction rate varies. This is evidenced not only by potentiodynamic cycling (that is, bursts of electrochemical noise) but also by acoustic emissions that may be observed during the pitting of aluminum. Currently, however, there is no method of correlating the electrochemical noise signals generated by the pitting process to pit initiation rates.

SUMMARY OF THE INVENTION

Accordingly, it is an object of the present invention to provide a method of determining pit initiation rates in an aluminum alloy.

Another object of the present invention to provide a method of electrochemical noise (ECN) data collection and analysis to determine pit initiation rates in an aluminum alloy.

It is a further object of the present invention to provide a method of ECN data collection that minimizes the amount of unwanted noise signals in order to maximize ECN data collection.

Other objects and advantages of the present invention will become more apparent hereinafter in the specification and drawings.

In accordance with the present invention, a method is provided for determining pit initiation rates of an aluminum alloy placed in an aqueous solution. A corrosion environment is created in the aqueous solution such that a pitting reaction occurs on the surface of the aluminum alloy. Electrochemical noise (ECN) signals produced by the resulting pitting reaction are then measured. The ECN signals are analog signals measured in the time domain. The ECN signals are then sampled resulting in a digitized ECN signal. A fast Fourier transform (FFT) is preformed on the digitized ECN signals to generate frequency spectrum amplitude data. Finally, the frequency spectrum amplitude data is converted to a log-log scale, whereby the pit initiation rate is directly proportional to the maximum-minimum spectral amplitude difference value.

DESCRIPTION OF THE PREFERRED EMBODIMENTS

Figure 2:
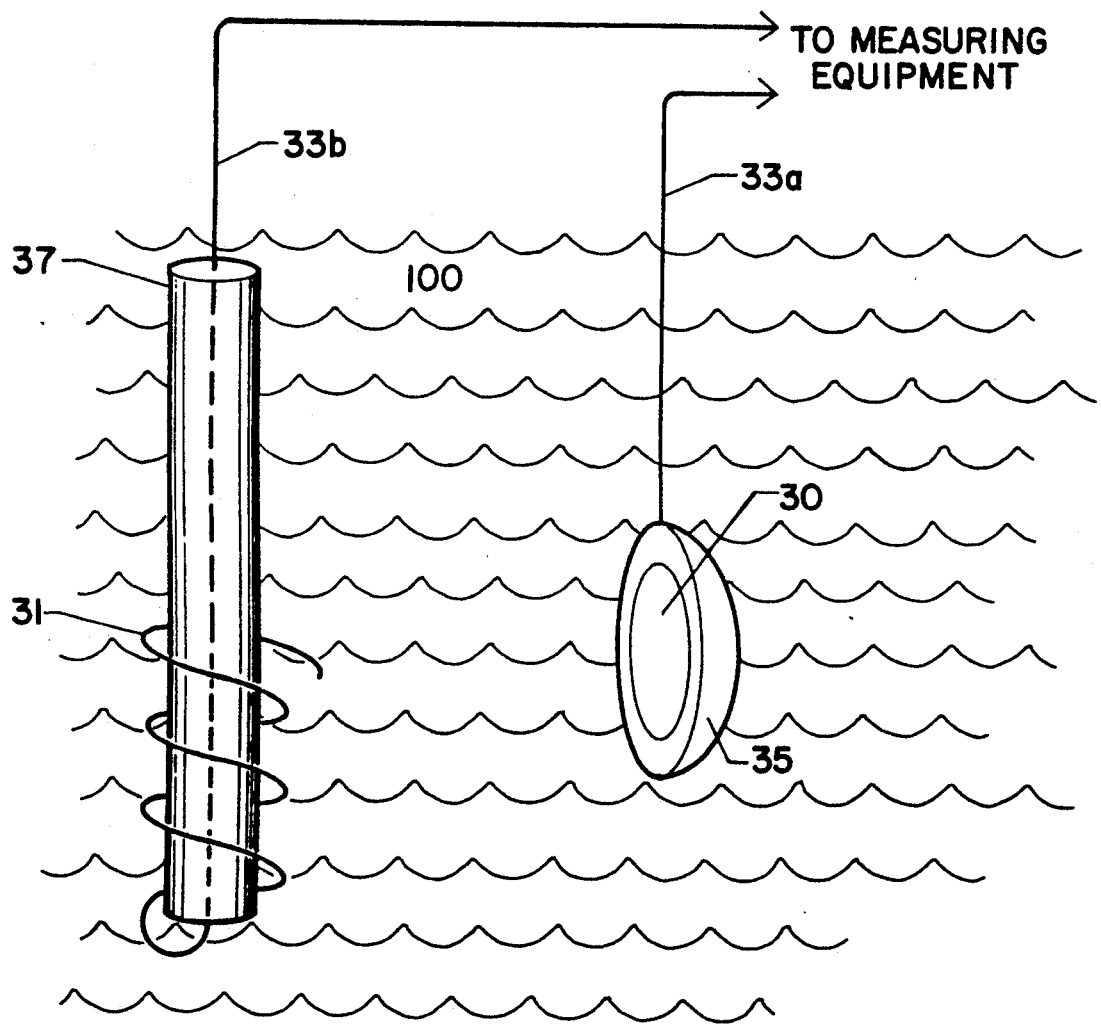
FIG. 2 is a schematic representation of an inert electrode in relationship to the aluminum alloy in the aqueous solution for measuring potential changes at the surface of the aluminum alloy according to the method of the present invention.

Accurate measurements of electrical potential fluctuation from a single corrosion pit cell on an aluminum sample surface are very difficult to obtain. However, the aggregate effect of all pitting on a surface can be easily measured. Referring now to FIG. 2, by coupling a sample 30 of an aluminum alloy to an inert electrode 31 exposed to the pitting solution 100 as shown in FIG. 2, potential changes at the sample surface may be measured. Inert electrode 31 is typically platinum wire. When in physical contact with the pitting solution 100, the inert electrode 31 serves as a conduit of electrons as well as a site for oxygen reduction. It also offers a convenient site from which to take potential measurements. Accordingly, sample 30 and inert electrode 31 are connected via electric wires 33a and 33b, respectively, to measuring equipment discussed later herein.

The technique used to induce a pitting reaction for measurement of ECN may be performed in one of two ways. A first method uses a potentiostat to electrolytically induce a pitting reaction while the second method allows the reaction to be induced naturally by a chemical environment. The problem with electrolytically inducing the pitting reaction is that instrumentation adds a significant amount of electronic noise which is superimposed onto the basic signal under observation. Sophisticated mathematical techniques must then be applied to screen out this instrument noise prior to data analysis. Additionally, the use of potentiostatic control during the pitting process interjects artificialities in the development of the aqueous solution/aluminum surface diffusion boundary. These artificialities skew predicted corrosion rates away from actual in situ values and probably alter some mechanisms of the pitting reaction. Accordingly, the method of the present invention uses a direct potential measurement technique for pitting corrosion induced naturally by the corroding environment. Not only does this approach simplify data collection and analysis but also gives a higher degree of confidence that the measured noise actually reflects events of the pitting process.

The pitting reaction was set up in a Model K47 corrosion cell, manufactured by EG & G PARC. For each experimental run, an aluminum 6061 alloy sample 30 was polished to a 600 grit finish and mounted into a specimen holder 35 which exposed one square centimeter of surface area to the pitting solution 100. The inert or platinum counter electrode 31 consisted of 0.8 millimeter diameter wire sealed in glass tubing 37 with a 10 centimeter length exposed to the solution. This exposed length was tightly coiled around the glass tubing 37. By coiling inert electrode 31, a constant electrode geometry is guaranteed for each experimental run. Of course, any other method of guaranteeing a constant electrode geometry may be used.

The four aqueous pitting solutions creating the corrosion environment consisted of 0.1 normal sodium chloride (NaCl), sodium fluoride (NaF), sodium bromide (NaBr) and sodium iodide (NaI) in de-ionized water. Additionally, a fifth solution consisted of pure de-ionized water. Data resulting from the pitting reactions due to these five aqueous solutions will be described further herein below in order to validate the method of the present invention.

Figure 3:
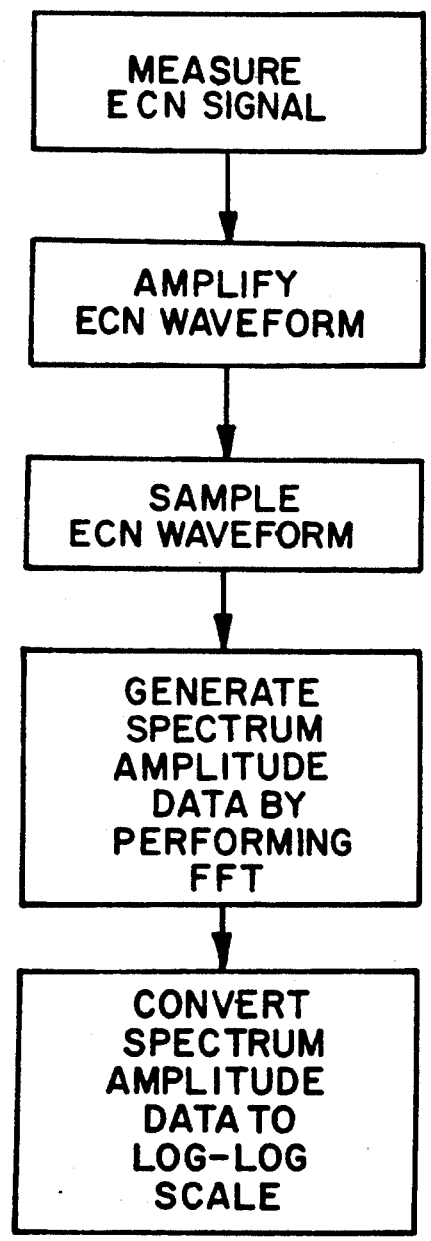
FIG. 3 is a flow diagram of the processing steps for the measured ECN according to the method of the present invention.

Referring again to FIG. 2, once the pitting reaction begins, potential changes generated at a pit cell on the surface of the aluminum alloy sample 30, as picked up by inert electrode 31, are processed as shown in the flow diagram of FIG. 3. The method of the present invention will be described for a pitting reaction occurring on the surface of separate aluminum 6061 alloy samples immersed in each of the five different aqueous solutions. For purposes of this description, each sample was immersed for one hour at 50° C. However, the method of the present invention is not limited thereto. The same method may be applied to any aluminum alloy for any length of time and at any temperature. Some design considerations affecting these variables might be the alloy used, the corrosion environment and/or the amount of time a sample will be exposed to a corrosion environment.

Each of the five solutions was raised to the testing temperature of 50° C. Then, before immersing the aluminum 6061 alloy sample into each solution, dry nitrogen gas was bubbled through each solution in order to provide a standardized gas content; that is, reducing the level of dissolved oxygen. Alternatively, any other inert gas such as helium may be used. Typically, this takes approximately 30 minutes. At this point, the aluminum 6061 alloy sample 30 in its specimen holder 35 as well as the platinum counter electrode 31 are immersed in each solution so that the ECN data collection and analysis may begin.

Referring again to FIG. 3, each ECN waveform is amplified and then sampled to produce a digitized ECN signal. Amplification is typically accomplished with a variable gain amplifier. Sampling of the ECN waveform could be accomplished by the connection of wires 33a and 33b with any conventional analog-to-digital converter (not shown), such as a Nicolet 9020 digital oscilloscope which is capable of capturing and storing sequential ECN waveforms for every data collection event.

For purposes of description only, the sampling interval was established so that the frequency range of 1 to 500 Hertz (Hz) could be examined. Sampling the signal at points too close together yields redundant data while sampling at points too far apart results in the loss of high frequency components. Using the Nyquist sampling criteria, the highest measurable frequency that can be resolved is given by $f_{max} = \frac{1}{2}t$ where t is the sampling interval. Similarly, the minimum frequency resolution is given by $f_{min} = 1/Nt$ where N is the number of samples per record. Using a sampling interval of one millisecond for 2048 points resulted in a $f_{max}$ of 500 Hz and $f_{min}$ of 0.49 Hz with the total record length of 2.048 seconds.

The digitized ECN signals are then used to generate amplitude spectrum data through Fourier analysis. This is accomplished by performing a fast Fourier transform (FFT) on the digitized ECN signals. Finally, the spectrum amplitude data is converted to a log-log scale that provides an indication of the pit initiation rates as will be described further hereinbelow. Performance of the FFT and conversion to the log-log scale was accomplished with the aid of the digital computer. A FFT is calculated for each of the stored ECN waveforms from a data collection event. Specifically, the mean value of each ECN waveform is determined. The mean value is then subtracted from the ECN waveform in order to remove any DC offset. The result is then divided by the amplifier gain in order to determine true waveform amplitudes. Finally, a FFT is performed on this actual waveform. Multiple FFT's for the same corrosion environment are then combined to produce a single average FFT. The averaging technique reduces spectral contributions of external noise and provides confidence as to repeatability of the data.

In order to assure that the noise measured is due only to electrochemical noise created by the pitting reaction, a number of shielding precautions must be taken. Some of these precautions include: 1) providing an electromagnetic shielded environment for the test set-up, and 2) using the shortest possible lengths of shielded coaxial cable between the corrosion cell, amplifier, oscilloscope and digital computer.

Figure 4:
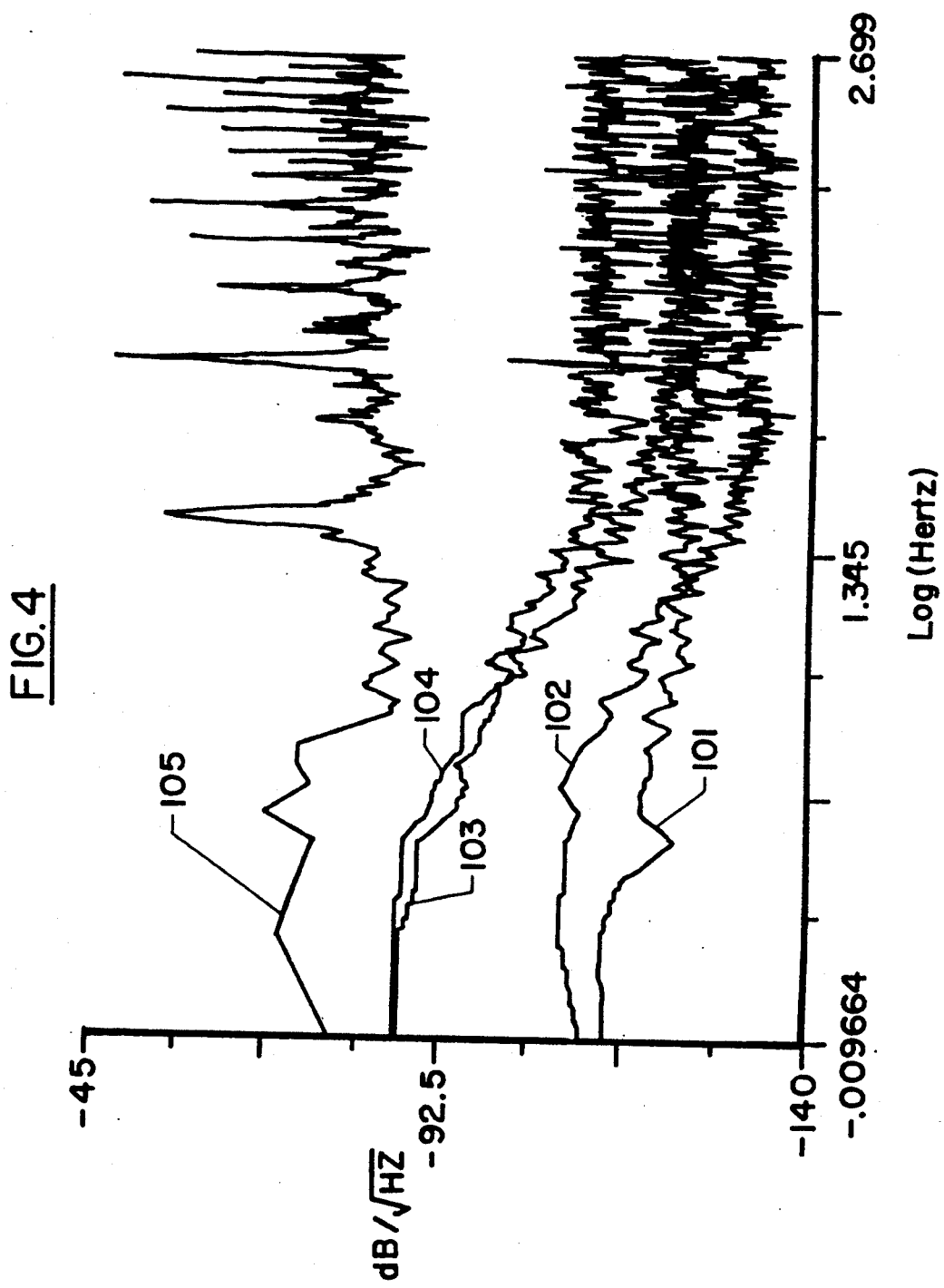
FIG. 4 is a composite log-log scale plot of the measured ECN from an aluminum 6061 sample immersed in five different aqueous solutions according to the method of the present invention.

Referring now to FIG. 4, a composite log-log scale plot is shown for an aluminum 6061 alloy sample immersed in each of the five different aqueous solutions. Each solution was maintained at 50° C. and each sample was allowed to react in the respective solutions for one hour. Each plot is the ECN measured at the end of one hour and is plotted on the same log-log scale. The horizontal axis is the log of the frequency range from 1 to 500 Hz. The vertical axis is the frequency amplitude of the ECN signal scaled in decibels (dB) divided by the square root of the frequency where dB = 20 log (voltage ratio). For purposes of the embodiment described, the voltage ratio is referenced to one volt.

The five plots in FIG. 4 are referenced as follows:
Plot 101 represents the sodium fluoride solution,
Plot 102 represents the sodium iodide solution,
Plot 103 represents the sodium bromide solution,
Plot 104 represents the sodium chloride solution, and
Plot 105 represents the pure de-ionized water solution.

In examining FIG. 4, several consistent characteristics of the electrochemical noise are immediately apparent. First, amplitude levels in the de-ionized water plot 105 are generally constant over the entire 1-500 Hz bandwidth at levels higher than those of the halide solution plots 101-104. Second, in all four halide solution plots 101-104, the ECN log-log scale frequency amplitudes are relatively high at low frequencies and decrease at an approximately linear rate on the log-log scale as frequency increases. This linear decrease is followed by a leveling-off of the amplitude values.

With respect to the amplitude of plot 105 for de-ionized water, ECN is consistently higher than that for any of the halide solutions across the 500 Hz bandwidth. Since a thicker oxide film 13 is anticipated in the de-ionized water environment, larger potentials across the film 13, and thus larger potential fluctuations, are expected. Similarly, with the thinner films associated with the halide environments, lower film potentials and fluctuations are expected. Both of these expectations are confirmed by the plots in FIG. 4. The passive nature of the de-ionized water environment supports large potential fluctuations thereby maintaining the film 13 in the passive region above the primary passive potential. The lower amplitude fluctuations associated with the halides imply more time during the cycle below the primary passive potential in the active region of the passivation curve and thus a higher corrosion rate.

Figure 1:
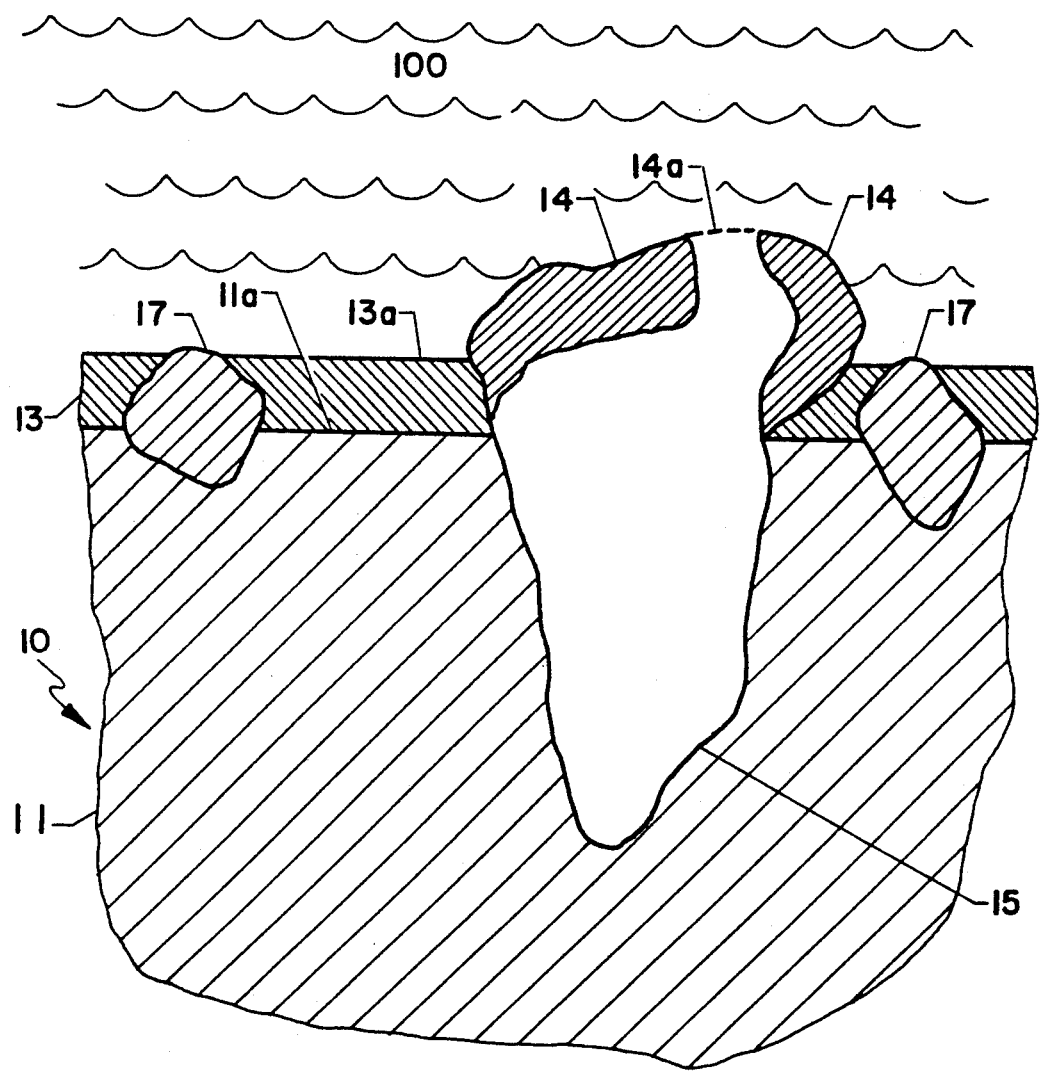
FIG. 1 is a cross-sectional, diagrammatic illustrative view of an established pitting corrosion cell present in an aluminum alloy exposed to an aqueous solution.

Referring again to FIG. 1, the ability of the oxide film 13 to repair and maintain itself is related to its ability to produce excess aluminum ions at the film surface 13a/aqueous solution 100 boundary. Accordingly, the greater the ECN noise amplitude produced by an alloy in a given environment the greater its pitting resistance. This is based on the assumption that the production and consumption of aluminum ions is a major contributor to changing the film potential characteristics. If more aluminum ions are available than are being consumed by the pitting reaction, the film becomes relatively thicker with correspondingly higher potential fluctuations. Similarly, a lesser ability to oxidize aluminum ions results in 1) all available aluminum ions being consumed by corrosion reactions, 2) thinner films, and 3) smaller potential fluctuations.

Since the dynamic film stabilization process occurring in de-ionized water is constant as evidence by constant spectral amplitudes across the spectral bandwidth in plot 105, balanced breakdown/repair reactions may be assumed to be taking place. If in changing the solution environment to one where pitting reactions are occurring (i.e., breakdown predominates over repair) as in the halide solutions, changes in spectral amplitudes are attributable to the predominance of the breakdown process. This is consistently shown in FIG. 4 for all four halide solutions.

The plots in FIG. 4 show higher spectral amplitudes at lower frequencies which decrease linearly on the log-log scale and stabilize at a low level for higher frequencies. This implies that the breakdown processes which predominate in a pitting environment are of a low-frequency nature evidenced by their higher amplitudes.

Figure 5:
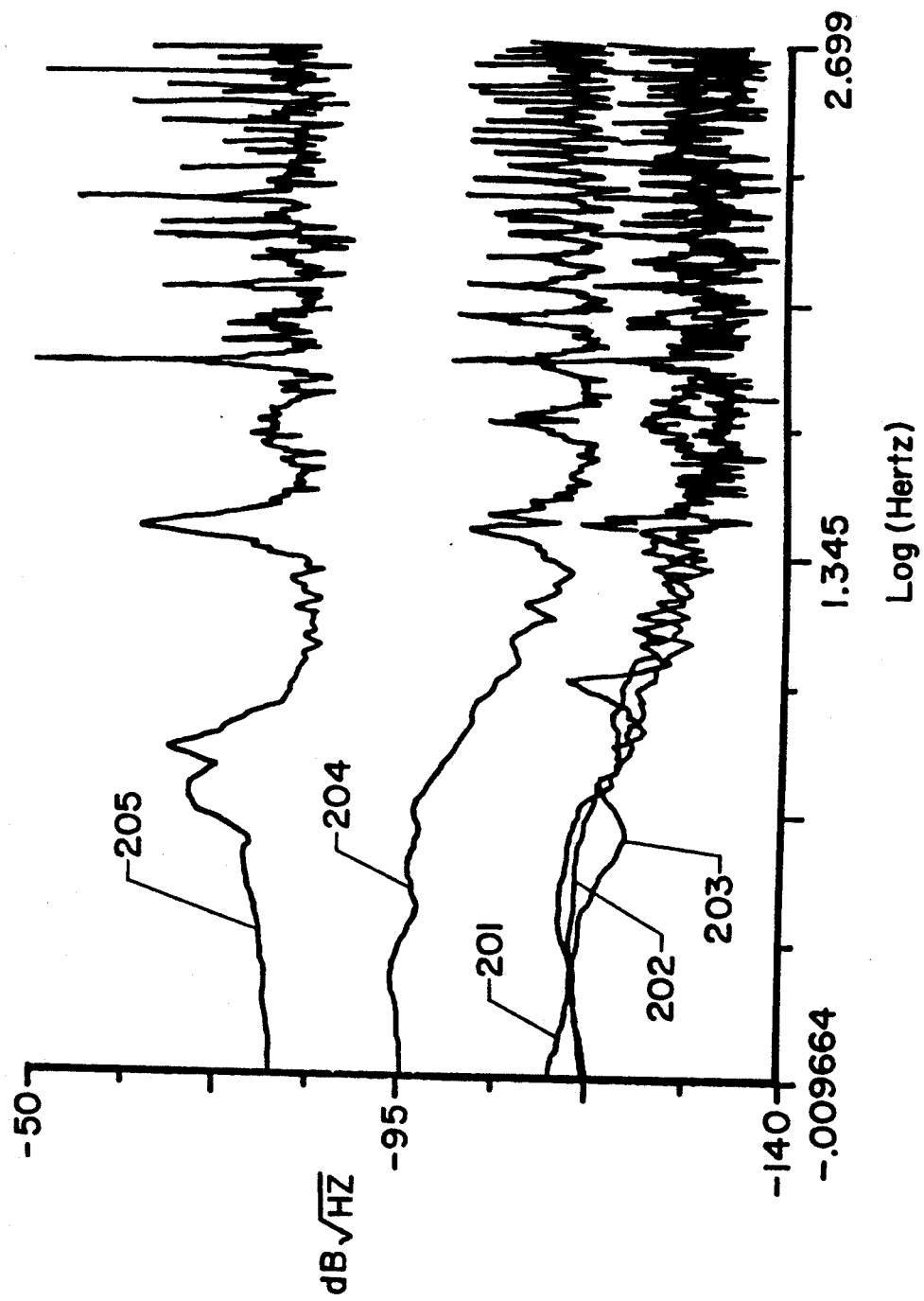
FIG. 5 is a composite log-log scale plot of the measured ECN of an aluminum 6061 sample immersed in the five aqueous solutions at 50° C. for three hours.
Figure 6:
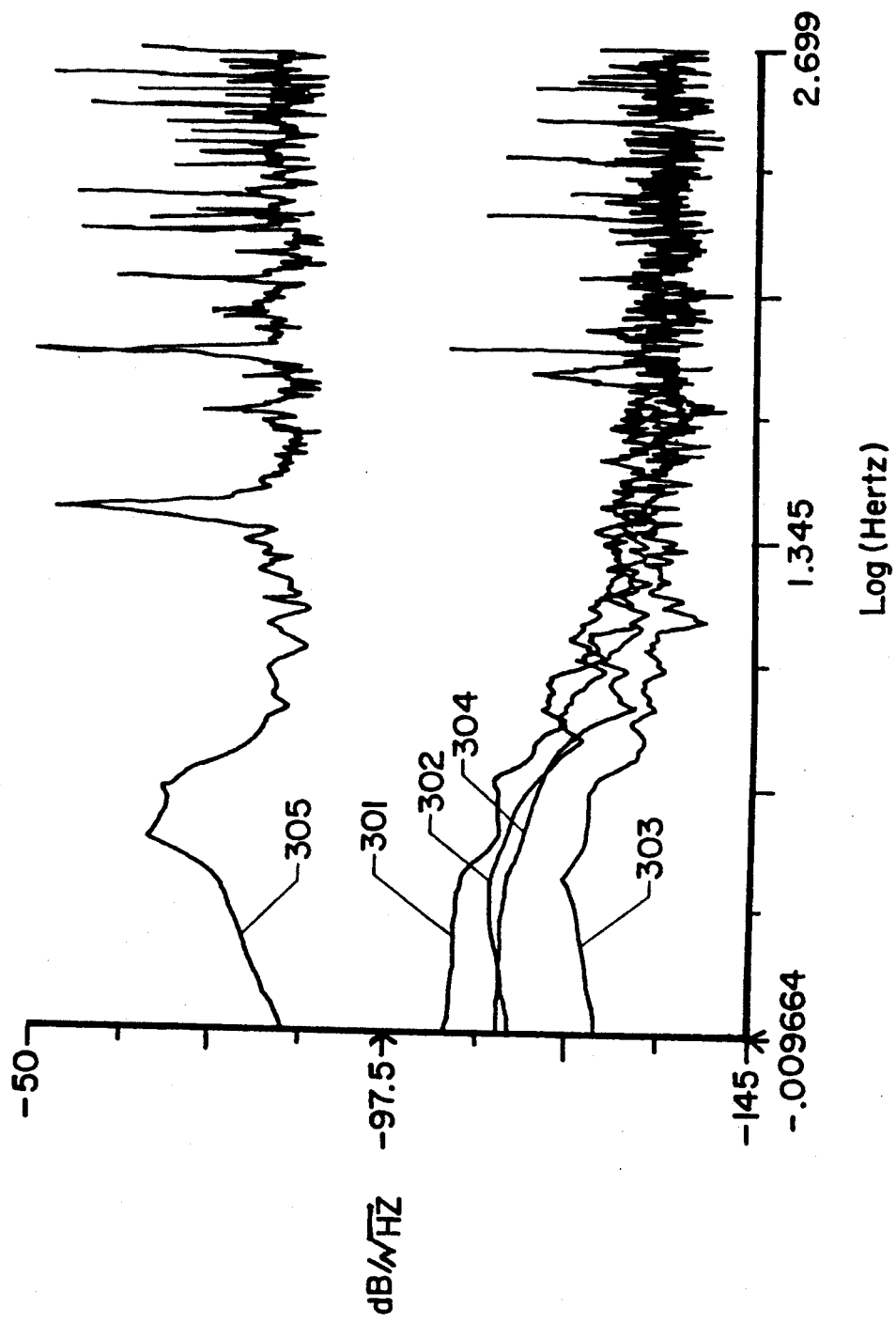
FIG. 6 is a composite log-log scale plot of the measured ECN of an aluminum 6061 sample immersed in the five aqueous solutions at 70° C. for one hour.

The differences between the maximum and minimum amplitude levels appear to be a reflection of the pit initiation rate associated with the respective halide environments. This hypothesis is supported by plot 104 in FIG. 4 where the highest values are associated with the solution containing chloride which is known to be the most aggressive pitting anion of the halide group. The amplitude max-min differential generally decreases with increasing time and temperature as shown in FIGS. 5 and 6. It will be appreciated that pit initiation rate decreases with increasing time due to consumption of reactants in a closed environment. It will also be appreciated that pit initiation rate decreases with increasing temperature due to increased thermal mixing, higher specie mobility, and film stress relief. The general decrease of the amplitude max-min differential with increasing time and increasing temperature which is observed in FIGS. 5 and 6 is consistent with these factors. FIG. 5 is a composite log-log scale plot of the measured ECN of an aluminum 6061 alloy sample immersed in the five aqueous solutions at 50° C. for 3 hours. Plots 201-205 correspond to the aqueous solutions used in plots 101-105, respectively. FIG. 6 is a composite log-log scale plot of the measured ECN of an aluminum 6061 alloy sample at 70° C. for one hour. Plots 301-305 correspond to the aqueous solutions used in plots 101-105, respectively.

The advantages of the present method are numerous. The method generates a plot indicative of pit initiation rates on the surface of an aluminum alloy based on measured ECN. The method minimizes the amount of external noise generation by utilizing a naturally induced corrosion environment and by shielding the test set-up from outside electronic noise.

Thus, it will be understood that many additional changes in the details, materials, steps and arrangement of parts, which have been herein described and illustrated in order to explain the nature of the invention, may be made by those skilled in the art within the principle and scope of the invention as expressed in the appended claims.

What is claimed is:

1. A method of determining pit initiation rates for an aluminum alloy in an aqueous solution, comprising the steps of:

providing an aqueous solution, said aqueous solution being a halide solution in de-ionized water, whereby a pitting reaction occurs on the surface of the aluminum alloy;

stabilizing the temperature of said aqueous solution;

bubbling dry inert gas through said temperature stabilized aqueous solution to provide a standardized gas content;

measuring electrochemical noise (ECN) signals in the time domain generated by the pitting reaction;

sampling said ECN signal in the time domain to create a digitized ECN signal;

processing said digital ECN signals to generate frequency spectrum amplitude data, including determining a mean value of each ECN signal, and thence subtracting each means value from each respective ECN signal whereby a DC offset is removed from each ECN signal, and thence performing a fast Fourier transform (FFT) after said step of subtracting; and converting said frequency spectrum amplitude data to a log-log scale wherein the difference between the maximum and minimum spectral levels at the two sides of the frequency spectrum range are indicative of the pit initiation rates.

2. A method according to claim 1 wherein said step of bubbling dry inert gas comprises bubbling dry nitrogen gas through said temperature stabilized aqueous solution.

3. A method according to claim 1 wherein said step of bubbling dry inert gas comprises bubbling dry helium gas through said temperature stabilized aqueous solution.

* * * * *